United States Patent [19]

Commandeur et al.

[11] Patent Number: 4,957,815
[45] Date of Patent: Sep. 18, 1990

[54] POLYARYLALKANE OLIGOMER COMPOSITIONS CONTAINING XYLENE UNITS, PROCESS FOR THEIR MANUFACTURE, AND PRODUCTS CONTAINING THE SAME

[75] Inventors: Raymond Commandeur, Vizile; Bernard Gurtner, Grenoble, both of France

[73] Assignee: Societe Atochem

[21] Appl. No.: 214,286

[22] Filed: Jul. 1, 1988

[30] Foreign Application Priority Data

Jul. 16, 1987 [FR] France ................................. 87 10068

[51] Int. Cl.$^5$ .......................... B01J 13/02; C07C 2/03; C07C 15/08; C07C 15/12
[52] U.S. Cl. .................. 428/402.2; 503/213; 585/11; 585/19; 585/25; 585/320; 585/326; 252/364
[58] Field of Search .................. 503/213; 252/364; 428/402.2; 585/7, 8, 19, 25, 320, 426

[56] References Cited

U.S. PATENT DOCUMENTS

| | | | |
|---|---|---|---|
| Re. 32,162 | 5/1986 | Sato et al. | 428/402.2 X |
| 3,846,331 | 11/1974 | Konishi et al. | 252/364 X |
| 3,865,613 | 2/1975 | Ross et al. | 503/213 |
| 3,936,566 | 2/1976 | Sato et al. | 503/213 |
| 4,039,712 | 8/1977 | Sato et al. | 503/213 |
| 4,130,299 | 12/1978 | Wygant | 503/213 |
| 4,390,194 | 6/1983 | Sato et al. | 503/213 |
| 4,523,044 | 6/1985 | Commandeur et al. | 585/19 X |
| 4,753,745 | 6/1988 | Kostusyk et al. | 585/25 X |
| 4,774,136 | 9/1988 | Okada et al. | 428/402.2 |
| 4,783,439 | 11/1988 | Usami et al. | 503/213 |
| 4,814,537 | 3/1989 | King | 585/426 X |
| 4,822,767 | 4/1989 | Okada et al. | 503/213 |

FOREIGN PATENT DOCUMENTS

| | | | |
|---|---|---|---|
| 8289 | 2/1974 | Japan | 503/213 |
| 164889 | 12/1981 | Japan | 503/213 |
| 11085 | 1/1982 | Japan | 503/213 |

*Primary Examiner*—Richard D. Lovering
*Assistant Examiner*—John Covert
*Attorney, Agent, or Firm*—Sigalos, Levine & Montgomery

[57] ABSTRACT

Polyarylalkane oligomer compositions consisting essentially of a mixture of isomers of xylyl-xylene and of higher homologues and a mixture of isomers of bis(-dimethylphenyl)xylylene and of higher homologues; the method of making such compositions by first reacting toluene, xylene, or a mixture of toluene and xylene with chlorine in the presence of a radical generator, removing the unreacted toluene, and then subjecting the reaction product to the action of an inorganic halide or inorganic acid in the presence of xylene, and microcapsules containing color-forming material wherein the compositions are used as solvents for the color-forming material.

5 Claims, No Drawings

POLYARYLALKANE OLIGOMER COMPOSITIONS CONTAINING XYLENE UNITS, PROCESS FOR THEIR MANUFACTURE, AND PRODUCTS CONTAINING THE SAME

BACKGROUND OF THE INVENTION

The present invention relates to new compositions of polyarylalkane oligomers containing xylene units, a process for their manufacture, and products utilizing such compositions.

These products can be used as a microencapsulation solvent for rupturable microcapsules used to make carbonless transfer paper and for other products for which microcapsules can be used.

In Patent EP No. 136,230, the person skilled in the art has already proposed mixtures of oligomers based on benzyltoluene, dibenzyltoluene and ditolylphenylmethane, which exhibit the advantage, when compared with these same oligomers taken separately, of crystallizing at very low temperature and of having a viscosity which is always compatible with their application as a dielectric for capacitors.

These characteristics make them most particularly suitable for use as a microencapsulation solvent for microcapsules for such uses as in making carbonless transfer paper. However, they have a characteristic which disqualifies them for such use; namely, a highly unpleasant odor which is disclosed just like the color when the microcapsules are ruptured, at the time of hitting the keys of a typewriter, for example. The compositions according to the present invention not only have a viscosity which is compatible with the application, but are also characterized by an "absence of odor" which is absolutely essential in the intended application as a microencapsulation solvent for forming microcapsules.

Patent GB No. 1,346,364 summarizes the properties which must be reconciled in microencapsulation solvents:

(i) dissolving the color-forming material, such as a dye,
(ii) not evaporating when the microcapsules are processed,
(iii) being inert towards the encapsulation material,
(iv) not reacting with the solvent developer,
(v) having a viscosity which is low and relatively insensitive to temperature, and
(vi) not having an unpleasant odor.

Since the disadvantages of mono- and dibenzylalkylbenzenes have also long been known, many substitute mixtures have been proposed, starting with polyarylalkane oligomers. However, it is always difficult to reconcile the quality of the properties of the products obtained with the economic aspect of the means for producing this substitute product.

Thus, U.S. Pat. No. 3,939,095 describes methylphenyl(2,5-dimethylphenyl)methane or 2-xylylparaxylene, the synthesis of which may be carried out by reaction of methylbenzyl chloride with para-xylene, followed by a separation to gain access to this oligomer in a pure form.

Lastly, in Japanese Patent Application JP-Kokai No. 73-86,612 reference is made to the use of, as a microencapsulation solvent of di(propylbenzyl)propylbenzene, the preparation of which calls for several stages with purifications at each stage and, consequently, in addition to the economic aspect, and just like the preceding patent, presents problems of effluent discharge and environmental problems.

As a general rule, the development of products which are particularly adapted for application as a microencapsulation solvent, for example, of the monoxylylxylene type, has met with success only through the use of relatively nonselective syntheses to obtain these products.

SUMMARY OF THE INVENTION

The present invention discloses products which are adapted for use as a microencapsulation solvent and which have the advantage of being capable of being manufactured in a simple manner.

The present invention relates to polyarylalkane oligomer compositions consisting essentially of; preferably consisting of, a mixture of at least one oligomer A and at least one oligomer B, wherein:

(a) the oligomer A is a mixture of isomers of formula:

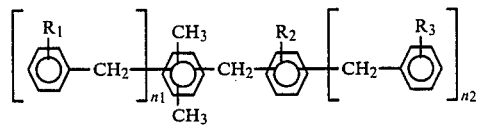

in which:

$R_1$, $R_2$ and $R_3$ are identical or different and selected from H or $CH_3$, and $n_1$ and $n_2$ each=0, 1 and 2, and $n_1+n_2 \leq 3$;

it being possible for each of the isomers A to have different substituents $R_1$, $R_2$ and $R_3$; and (b) the oligomer B is a mixture of isomers of formula:

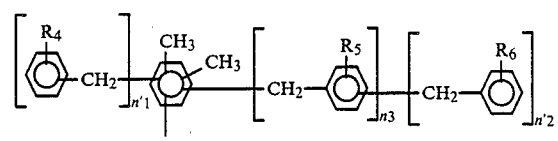

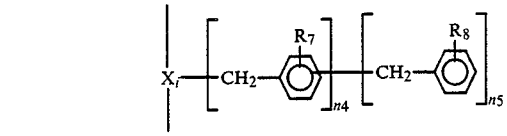

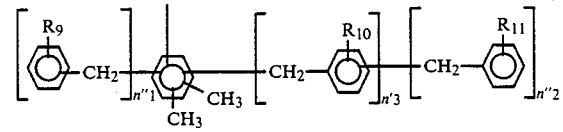

in which:

$R_4$, $R_5$, $R_6$, $R_7$, $R_8$, $R_9$, $R_{10}$ and $R_{11}$ are identical or different and selected from H or $CH_3$, $n'_1$, $n''_1$ and $n_4$ each=0, 1 or 2, $n'_2$, $n''_2$, $n_3$, $n'_3$ and $n_5$ each=0 or 1, $n'_1+n''_1+n'_2+n''_2+n_3+n'_3+n_4+n_5 \leq 2$, i has the value of 1 or 2, $X_i$ is a trivalent connecting group such as:

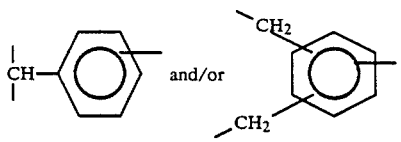 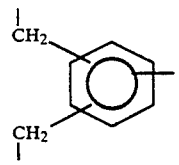

and in which the connections towards the groups

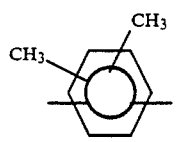

are provided by carbon a not forming part of the phenyl group of $X_i$;

each of the isomers B having the same or different substituents $R_4$ to $R_{11}$.

That is to say, B may be a mixture of the products of formula (I) and (II) below, each of the products (I) and (II) itself being a mixture of isomers.

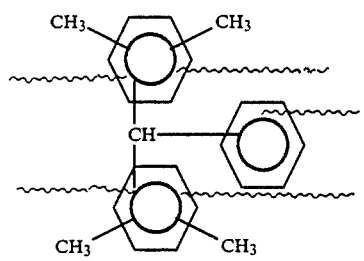

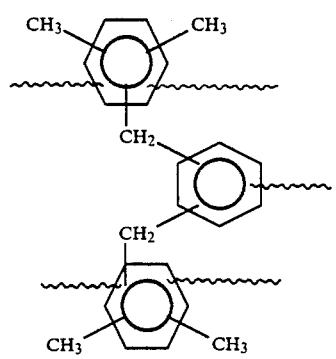

Compositions in which $R_1$ to $R_{11}$ are $C_3$ groups are advantageously employed.

Compositions in which $X_i$ is

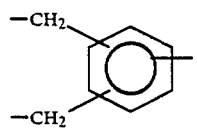

are also advantageously employed.

The preferred compositions are such that $R_1$ to $R_{11}$ are $CH_3$ groups and $X_i$ is The compositions according to the invention exhibit all the properties which must be reconciled in microencapsulation solvents and it has been surprisingly found that these products are not odorants. The invention also comprises the process of making the compositions as hereinafter set forth and microcapsules containing the same.

DETAILED DESCRIPTION

A process for the manufacture of the compositions of polyarylalkane oligomers according to the invention is characterized in that, in a first stage, chlorine is reacted with toluene, xylene, or a mixture of toluene and xylene in the presence of a radical generator, and then any unreacted toluene is removed and in that, in a second stage, the reaction product from this first stage is subjected to the action of an inorganic halide or of an inorganic acid in the presence of xylene.

The starting hydrocarbon in the first stage is preferably either xylene or a mixture of toluene and xylene.

The radical chlorination of the hydrocarbon is usually carried out at a temperature of between 50° and 110° C. and, better, between 70° and 100° C. It is preferably conducted so that only 10 to 50%, expressed as a molar percentage, of the hydrocarbon employed is converted into the corresponding chlorine derivative. The unreacted toluene is then removed, for example, by distillation. The free radical generator employed may be either a photochemical initiation or a chemical initiator. Among the chemical initiators there may be mentioned azo compounds such as azodiisobutyronitrile or else azodivaleronitrile, and peroxides such as, for example, lauroyl peroxide The quantity of chemical initiator which is employed is generally between 0.05 and 3% by weight relative to the hydrocarbon employed, and preferably between 0.1 and 1.5%.

The reaction mixture obtained during the first stage is then subjected, in the presence of xylene, to the action of an inorganic halide, or else of an inorganic acid. In practice, this reaction takes place at a temperature of between 30° and 140° C., and preferably between 50° and 120° C.

If the hydrocarbon in the first stage contains xylene, there is no need to add it during the second stage.

Xylene is advantageously added to the mixture obtained at the end of the first stage after the removal of any toluene.

Preferably, as many moles of xylene are added as are removed in the form of any toluene.

Among the inorganic halides, it is possible to employ ferric chloride, antimony trichloride, titanium tetrachloride or else aluminum chloride in weight concentrations, relative to the reaction mixture, which are generally between 50 ppm and 1%, and preferably between 100 ppm and 0.5%. Inorganic acids may also be employed, for example, sulphuric acid at a concentration of between 70 and 95% by weight. It is also possible to employ zeolites or, alternatively, certain inorganic oxides. An alternative form of the process in this second stage consists in pouring the reaction mixture from the first stage into xylene, or xylene and the mixture of oligomers according to the invention, containing the inorganic halide or acid in the form of a solution or a dispersion. This alternative form is particularly advantageous for operating a continuous process of this kind, since it is obvious that this synthesis can be carried out noncontinuously or continuously.

After the excess xylene has been distilled off, the removal of the inorganic halide or of the inorganic acid may be carried out by any known method such as washing with water, neutralizing and drying.

Xylene is advantageously employed in the first stage, and the groups $R_1$ to $R_{11}$ (in the compositions according to the invention) are then methyl groups, and $X_i$ is

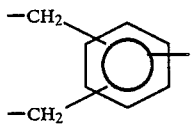

The xylene employed may be the mixture of isomers or the isomers taken separately or, alternatively, combinations 2 by 2.

According to the process described, the mixture of polyarylalkane oligomers is generally obtained directly in the following proportions by weight:

A as a mixture of isomers:
$n_1+n_2=0$, between 56 and 90%,
$n_1+n_2=1$, between 7 and 28%,
$n_1+n_2=2$, between 1.5 and 8%, and
$n_1+n_2=3$, between 0.1 and 2%.

B as a mixture of isomers:
$n'_1+n''_1+n'_2+n''_2+n_3+n'_3+n_4+n_5=0$, between 1.1 and 10%,
$n'_1+n''_1+n'_2+n''_2+n_3+n'_3+n_4+n_5=1$, between 0.025 and 3%, and
$n'_1+n''_1+n'_2+n''_2+n_3+n'_3+n_4+n_5=2$, between 0.05 and 1%.

Depending on the use to which the mixture of polyarylalkane oligomers according to the invention is applied, it may be advantageous to perform a flash evaporation of this mixture to remove traces of impurities originating either from the starting materials or from the process, or having an incidental origin; in all cases their contents by weight do not exceed 1 to 2%. Among the pieces of equipment which can be employed, preference will be given to a thin-film evaporator. It must be reported, however, that, on an industrial scale, the technical performance of such equipment in respect of behavior under vacuum does not always allow all of the mixture of polyarylalkane oligomers to be recovered. These evaporated products nevertheless form an integral part of the invention, as is the case particularly with the isomers of the compound A for $n_1+n_2=3$ and of the compound B for $n'_1+n''_1+n'_2+n''_2+n_3+n'_3+n_4+n_5=2$.

The oligomer compositions of the present invention can be used to form microcapsules, such as for use in making carbonless transfer paper, by using the compositions to dissolve the dye or other color-forming material requiring dissolving to be utilized, and forming the microcapsules in any conventional manner using conventional proportions of materials and reaction conditions. The oligomer compositions are used in those amounts necessary to properly dissolve the color-forming material. The outer rupturable encapsulating material can be any conventionally used for this purpose.

The invention will be further described in connection with the following examples which are set forth for purposes of illustration only.

EXAMPLE 1

424 g of ortho-xylene (4 moles) are placed in a reactor equipped with stirring means, a condenser, a chlorine feed tube and a Philips TLADK 30-watt lamp. 71 g of gaseous chlorine (1 mole) are then introduced while the temperature is maintained at 80° C. for 1 hour.

After stopping the photochemical initiation, the reaction mixture is placed in a dropping funnel and is introduced over 1 hour into a reactor equipped with stirring means, containing 2 moles of ortho-xylene and 60 mg of $FeCl_3$, at a temperature of 100° C. The whole is kept at 100° C., with stirring, for another one hour after the end of addition. After cooling, the reaction mixture is washed with 10% hydrochloric acid and then with water until neutral. The excess ortho-xylene is removed by distillation under a vacuum of 10 mm of mercury (1330 Pa) through a column of a few plates, to ensure that the residual content of o-xylene in the bottom product is below 500 ppm (bottom temperature at the end of distillation $=190°$ C.).

The mixture of polyarylalkane oligomers which is obtained is such that in the general formula $R_1$ to $R_{11}$ are $CH_3$ groups and $X_i$ is:

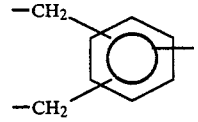

The mixture of polyarylalkane oligomers which is obtained has the following composition by weight:

| PRODUCT | $n_1 + n_2$ | | | | $n'_1 + n''_1 + n'_2 + n''_2 + n_3 + n_4 + n_5$ | | |
|---|---|---|---|---|---|---|---|
| | 0 | 1 | 2 | 3 | 0 | 1 | 2 |
| A | 73 | 14.6 | 3.7 | 1.7 | — | — | — |
| B | — | — | — | — | 5.4 | 1.3 | 0.3 |

The weight yield calculated on o-xylene consumed is 97%.

When subjected to a flash evaporation at 300° C. at 0.5 mm Hg (66 Pa), this product gives, in 96% yield, a mixture of polyarylalkane oligomers with a very weak odor, in which the only difference from the composition given above is the absence of the products corresponding to:
(i) A and $n_1+n_2=3$, and
(ii) B and $n'_1+n''_1+n'_2+n''_2+n_3+n'_3+n_4+n_5=2$.
The viscosity at:
(i) 20° C. is 34.4 cP (34.4 m Pa s), and
(ii) 40° C. is 12.3 cP (12.3 m Pa s).

EXAMPLE 2

Operating under the same conditions of Example 1, but using 6 moles of o-xylene (592 g) in the photochlorination per 1 mole of chlorine introduced and 4 moles of o-xylene in the coupling reaction. The mixture of polyarylalkane oligomers which is obtained has the same formula as in Example 1, and has the following composition by weight:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 82 | 8.3 | 3.4 | 1.3 | — | — | — |
| B | — | — | — | — | 4 | 0.8 | 0.2 |

The weight yield calculated on the o-xylene which has reacted is 97%.

The viscosity is as follows:
40° C. = 9.9 cP
20° C. = 25.8 cP

When subjected to a flash evaporation at 300° C. at 0.5 mm Hg, (66 Pa), this product gives, in a 98% yield, a mixture of polyarylalkane oligomers with a very faint odor and whose composition differs from that given above in the absence of the products corresponding to:
(i) A and $n_1+n_2=3$, and
(ii) B and $n'_1+n''_1+n'_2+n''_2+n_3+n'_3+n_4+n_5=2$.
For a viscosity:
(i) at 20° C. = 18.4 cP (18.4 m Pa s), and
(ii) at 40° C. = 7.6 cP (7.6 m Pa s)

EXAMPLE 3

Operating under the same conditions as Example 1, but using 2 moles of ortho-xylene for the photochlorination per 1 mole of chlorine introduced and retaining 2 moles of oxylene for the coupling reaction.

The mixture of polyarylalkane oligomers which is obtained has the same formula as in Example 1 and has the following composition by weight:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 63 | 17.3 | 7.2 | 1.3 | — | — | — |
| B | — | — | — | — | 8.2 | 2.6 | 1 |

The weight yield based on the ortho-xylene which has reacted is 98%.

When subjected to a flash evaporation at 300° C. at 0.5 mm Hg (66 Pa), this product gives, in a yield of 98%, a mixture of polyarylalkane oligomers with a very faint odor and whose composition differs from that given above in the absence of the products corresponding to:
(i) A and $n_1+n_2=3$, and
(ii) B and $n'_1+n''_1+n'_2+n''_2+n_3+n'_3+n_4+n_5=2$.
For a viscosity:
(i) at 20° C. = 48.1 cP (48.1 m Pa s), and
(ii) at 40° C. = 19.6 cP (19.6 m Pa s)

EXAMPLE 4

Identical with Example 1 but replacing ortho-xylene with para-xylene.

The mixture of polyarylalkane oligomers which is obtained, with a faint odor, has the same formula as in Example 1 and has the following composition by weight:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 65 | 20.5 | 4.5 | 1.9 | — | — | — |
| B | — | — | — | — | 6 | 1.8 | 0.3 |

The weight yield based on the para-xylene which has reacted is 98%.

EXAMPLE 5

Identical with Example 1 but replacing ortho-xylene with meta-xylene.

The mixture of polyarylalkane oligomers which is obtained, with a faint odor, has the same formula as in Example 1 and has the following composition by weight:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 68 | 18.5 | 4.2 | 1.8 | — | — | — |
| B | — | — | — | — | 5.7 | 1.5 | 0.3 |

The weight yield based on the meta-xylene which has reacted is 98%.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A polyarylalkane oligomer composition consisting essentially of a mixture of at least one oligomer A and at least one oligomer B, wherein:
   (a) the oligomer A is a mixture of isomers of formula:

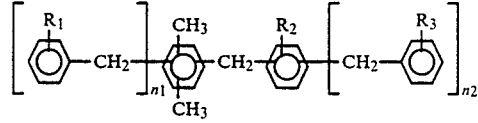

in which:
$R_1$, $R_2$ and $R_3$ are identical or different and selected from H or $CH_3$, and
$n_1$ and $n_2$ each $=0$, 1 and 2, and $n_1+n_2 \leq 3$;
each of the isomers A having the same or different substituents $R_1$, $R_2$ and $R_3$; and
   (b) the oligomer B is a mixture of isomers of formula:

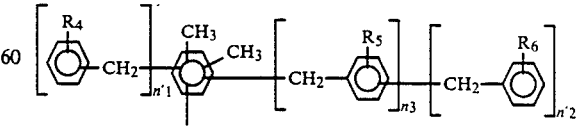

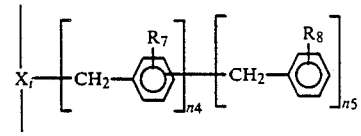

-continued

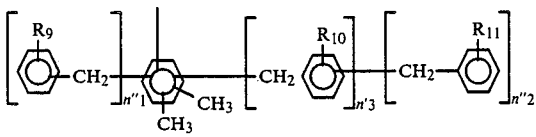

in which:
$R_4$, $R_5$, $R_6$, $R_7$, $R_8$, $R_9$, $R_{10}$ and $R_{11}$ are identical or different and selected from H or $CH_3$,
$n'_1$, $n''_1$ and $n_4$ each $= 0$, 1 or 2,
$n'_2$, $n''_2$, $n_3$, $n''_3$ and $n_5$ each $= 0$ or 1,
$n'_1 + n''_1 + n'_2 + n''_2 + n_3 + n''_3 + n_4 + n_5 \leq 2$,
i has the value of 1 or 2,
$X_i$ is a trivalent connecting group such as

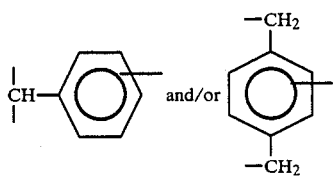

and in which the connections towards the groups

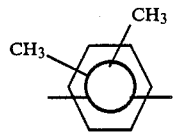

are provided by carbon atoms not forming part of the phenyl group of $X_1$;
each of the isomers B having the same or different substituents $R_4$ to $R_{11}$.

2. The composition according to claim 1, wherein $R_1$ to $R_{11}$ are $CH_3$ groups.

3. The composition of claim 2, wherein $X_i$ is:

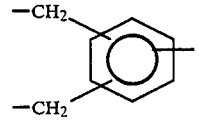

4. The composition of claim 3, wherein the mixture of oligomers is in the proportions by weight of:
(a) Compound A as a mixture of isomers:
$n_1 + n_2 = 0$, between 56 and 90%,
$n_1 + n_2 = 1$, between 7 and 28%,
$n_1 + n_2 = 2$, between 1.5 jand 8%, and
$n_1 + n_2 = 3$, between 0.1 and 2%; and
(b) Compound B as a mixture of isomers:
$n'_1 + n''_1 + n'_2 + n''_2 + n_3 + n'_3 + n_4 + n_5 = 0$, between 1.1 and 10%,
$n'_1 + n''_1 + n''_2 + n''_2 + n_3 + n''_3 + n_4 + n_5 = 1$, between 0.25 and 3%, and
$n'_1 + n''_1 + n'_2 + n''_2 + n_3 + n'_3 + n_4 + n_5 = 2$ between 0.05 and 1%.

5. Microcapsules comprising an outer rupturable encapsulating material and encapsulated therein a color-forming material and a solvent therefor, said solvent being the composition position of any one of claims 1 to 4.

* * * * *